United States Patent
Klarner (10) Patent No.: US 10,306,746 B2
(45) Date of Patent: May 28, 2019

(54) CYCLOTRON RF RESONATOR TUNING WITH ASYMMETRICAL FIXED TUNER

(71) Applicant: Varian Medical Systems Particle Therapy GmbH, Troisdorf (DE)

(72) Inventor: Fabian Klarner, Troisdorf (DE)

(73) Assignee: Varian Medical Systems Particle Therapy GmbH, Troisdorf (DE)

( * ) Notice: Subject to any disclaimer, the term of this patent is extended or adjusted under 35 U.S.C. 154(b) by 14 days.

(21) Appl. No.: 15/399,528

(22) Filed: Jan. 5, 2017

(65) Prior Publication Data

US 2018/0192506 A1 Jul. 5, 2018

(51) Int. Cl.
| | |
|---|---|
| *H05H 7/08* | (2006.01) |
| *H05H 7/02* | (2006.01) |
| *H05H 13/00* | (2006.01) |
| *A61N 5/10* | (2006.01) |
| *H05H 7/18* | (2006.01) |

(52) U.S. Cl.
CPC .............. *H05H 7/02* (2013.01); *A61N 5/1077* (2013.01); *H05H 7/08* (2013.01); *H05H 7/18* (2013.01); *H05H 13/005* (2013.01); *A61N 2005/1087* (2013.01); *A61N 2005/1095* (2013.01); *H05H 2007/025* (2013.01); *H05H 2007/082* (2013.01)

(58) Field of Classification Search
CPC ...... H05H 13/02; H05H 13/04; H05H 13/005; H05H 2007/043; H05H 2007/122; H05H 2007/007; H05H 7/02; H05H 2007/082; H05H 2007/025; H05H 7/001; H05H 7/08; A61N 5/1077; A61N 2005/1087; A61N 2005/1095
See application file for complete search history.

(56) References Cited

U.S. PATENT DOCUMENTS 3,868,522 A * 2/1975 Bigham ................. H05H 13/00
  313/62
4,139,777 A 2/1979 Rautenbach
(Continued)

FOREIGN PATENT DOCUMENTS

| CN | 106231774 | 12/2016 |
| CN | 106231775 | 12/2016 |
| JP | 2014160613 | 9/2014 |

OTHER PUBLICATIONS

Vasile Sabaiduc, Resonator Systems for the Best 70 Mev Cyclotron, 20 International Conference on Cyclotron and their Applications, Mar. 1, 2014.
(Continued)

*Primary Examiner* — Douglas W Owens
*Assistant Examiner* — Amy X Yang (57) ABSTRACT

Embodiments of the present invention disclose methods and systems for performing particle acceleration using a cyclotron RF resonator with an asymmetrical fixed tuner. A cyclotron RF resonator includes a single shorting plate tuner inside and a fixed short stem, and does not require top-bottom mirror symmetry. Small movements in relation to the wavelengths of the maximum acceleration voltage is bound by the capacitance of the accelerating surfaces. As such, the resonator may perform particle acceleration using asymmetrical tuning to reduce design complexity, cost of maintenance, fabrication and installation complexity, failure rate, and software complexity (e.g., control software), for example.

24 Claims, 7 Drawing Sheets

(56) References Cited

U.S. PATENT DOCUMENTS

| | | | | |
|---|---|---|---|---|
| 4,728,910 | A | * | 3/1988 | Owens .................... H01P 7/06 219/693 |
| 6,262,638 | B1 | * | 7/2001 | Scherer .................. H05H 5/08 250/492.21 |
| 2012/0161671 | A1 | | 6/2012 | Eriksson et al. |
| 2013/0106315 | A1 | * | 5/2013 | Abs ........................ H05H 7/02 315/502 |
| 2014/0094638 | A1 | * | 4/2014 | Gall ....................... H05H 7/12 600/1 |

OTHER PUBLICATIONS

Rodman Smythe, A Fractional Turn Injector Cyclotron, Procedings of the Fifth International Cyclotron Conference, Jan. 1, 1971, pp. 95-100.

\* cited by examiner

PRIOR ART

| Evaluation case | unfixed tuners | | | | | |
|---|---|---|---|---|---|---|
| Setpoint Asum | *0.51 V* | *deviation* | *0.69 V* | *deviation* | *0.78 V* | *deviation* |
| | V | % | V | % | V | % |
| Dee1 | 0,5128 | 0,1074 | 0,6931 | 0,0614 | 0,7829 | 0,0991 |
| Dee 2 | 0,5123 | 0,0098 | 0,6929 | 0,0325 | 0,7821 | -0,0032 |
| Dee 3 | 0,5125 | 0,0488 | 0,6925 | -0,0253 | 0,7816 | -0,0671 |
| Dee 4 | 0,5114 | *-0,1659* | 0,6922 | -0,0686 | 0,7819 | -0,0288 |
| average Dee voltage | 0,5123 | | 0,6927 | | 0,7821 | |
| Evaluation case | fixed tuners | | | | | |
| Setpoint Asum | *0.51 V* | *deviation* | *0.69V* | *deviation* | *0.78V* | *deviation* |
| | V | % | V | % | V | % |
| Dee1 | 0,5113 | -0,0782 | 0,6911 | -0,0761 | 0,7833 | 0,0687 |
| Dee 2 | 0,5113 | -0,0782 | 0,6914 | -0,0342 | 0,7819 | -0,1048 |
| Dee 3 | 0,5121 | 0,0782 | 0,6917 | 0,0033 | 0,7825 | -0,0326 |
| Dee 4 | 0,5121 | 0,0782 | 0,6924 | *0,1070* | 0,7833 | 0,0687 |
| average Dee voltage | 0,5117 | | 0,6917 | | 0,7827 | |
| Evaluation case | asymetrically fixed tuners | | | | | |
| Setpoint Asum | *0.51V* | *deviation* | *0.69V* | *deviation* | *0.78V* | *deviation* |
| | V | % | V | % | V | % |
| Dee1 | 0,5107 | -0,0091 | 0,6907 | -0,0387 | 0,780594 | -0,0519 |
| Dee 2 | 0,5106 | -0,0228 | 0,69041 | -0,0807 | 0,780533 | -0,0597 |
| Dee 3 | 0,5104 | -0,0678 | 0,69135 | 0,0554 | 0,78107 | 0,0091 |
| Dee 4 | 0,5112 | 0,0996 | 0,69141 | 0,0640 | 0,7818 | *0,1025* |
| average Dee voltage | 0,5107 | | 0,6910 | | 0,7810 | |

FIG. 5

| Fixed Tuners | | Symmetrically | Asymmetrically $\Delta b_{top}$= +5mm |
|---|---|---|---|
| | | Position | Position |
| | | mm | mm |
| Dee 1 | Top | 120,2006 | 125,2006 |
| | Bottom | 120,2006 | 115,2006 |
| Dee 2 | Top | 128,9681 | 133,9681 |
| | Bottom | 128,9681 | 123,9681 |
| Dee 3 | Top | 103,4777 | 108,4777 |
| | Bottom | 103,4777 | 98,4777 |
| Dee 4 | Top | 124,8339 | 129,8339 |
| (Coupler) | Bottom | 144,8339 | 139,8339 |

FIG. 6A

| ASUM = 0.51 | | Position | rel. Pos to Dee1 | Pickup Voltage | Asum (calc) |
|---|---|---|---|---|---|
| Temp Dee3 Up Tail / ° | 30,2 | mm | mm | V | V |
| Dee 1 | Top | 125,2174 | 0 | 0,51066 | |
| | Bottom | 115,2006 | | | |
| Dee 2 | Top | 133,9541 | 8,7367 | 0,51059 | |
| | Bottom | 123,9681 | | | 0,51070625 |
| Dee 3 | Top | 108,4777 | | | |
| | Bottom | 98,9809 | -16,2365 | 0,51036 | |
| Dee 4 | Top | 129,6685 | 4,4511 | 0,511215 | |
| (Coupler) | Bottom | 139,8339 | | | |

CYCLOTRON RF RESONATOR TUNING WITH ASYMMETRICAL FIXED TUNER

FIELD

Embodiments of the present invention generally relate to the field of cyclotron resonators. More specifically, embodiments of the present invention relate to systems and methods for tuning RF cyclotron resonators.

BACKGROUND

Standard radiation therapy using X-ray beams deposit their energy along the path of the beam to a target tumor. Particle therapy with protons or other ions is a type of radiotherapy that uses an external beam to provide targeted ionizing radiation to a tumor. Protons or other charged ions are sent to an accelerator to bring the particles' energy to a predetermined value. The protons or other ions then move through a beam-transport system, where magnets are used to shape, focus and/or direct the proton or other ion beam as necessary.

Traditionally, one of the key design aspects of particle therapy is the use of symmetrical tuners in a cyclotron resonator. The cavities of cyclotrons, called Dees, are tuned for matching the cavity eigenmode to the RF-Signal of the RF-Power supply system and to preserve the field balance between the cavities. Some proton therapy systems use Hill-Number Ford rotational symmetry. In addition, all cyclotron are designed to obtain Top-Bottom mirror symmetry, where the mirror plane coincides with the beam plane. A RF resonator is used to produce a voltage to accelerate particles. Within the resonator tuners are used to control the resonance frequency. The maximum accelerating voltage is expected to be in the middle of the distance between two tuners. If only one of the tuners is moved, the maximum accelerating voltage moves away from the median plane which negatively affects acceleration performance of a cyclotron.

The complexity of the cyclotron is increased greatly when both tuners need to be moved to maintain symmetry. For example, moveable sliding seals are used to separate atmospheric pressure from evacuated portions of the cyclotron. The use of a great number of moving parts increases the design complexity and the risk of failure of a moving part. Additionally, cyclotrons having symmetrical tuners require complex control software, especially when feedback loop algorithms are used for multi-dee cyclotrons. What is needed is a simplified high performance cyclotron that does not require complex control software and moving parts to reduce material, operation, and service costs of the cyclotron.

SUMMARY

Methods and systems for tuning a cyclotron resonator using asymmetrical tuners are disclosed herein.

According to one disclosed embodiment, a cyclotron is disclosed. The cyclotron includes a main coil for producing a magnetic field, an iron magnet surrounding the main coil for shaping the magnetic field, and a radio frequency resonator for producing an alternating electric field using the vacuum chamber. The resonator includes, a fixed short stem coupled to a vacuum chamber disposed within the cyclotron, a movable short stem coupled to the vacuum chamber, and a tuner plate disposed within the movable short stem, where the tuner plate asymmetrically tunes the RF resonator to accelerate particles.

According to another disclosed embodiment, fixed short stem for tuning an RF cyclotron resonator is disclosed. The fixed short stem includes a first shorting plate disposed within the fixed short stem, and an inner conductor disposed within the fixed short stem and in contact with the shorting plate. The inner conductor contacts an outer surface of a dee, a moveable short stem comprising a second shorting plate tunes the resonator by changing a distance between the second shorting plate and the first shorting plate, and the dee performs particle acceleration.

BRIEF DESCRIPTION OF THE DRAWINGS

The accompanying drawings, which are incorporated in and form a part of this specification, illustrate embodiments of the invention and, together with the description, serve to explain the principles of the invention.

DETAILED DESCRIPTION

Reference will now be made in detail to several embodiments. While the subject matter will be described in conjunction with the alternative embodiments, it will be understood that they are not intended to limit the claimed subject matter to these embodiments. On the contrary, the claimed subject matter is intended to cover alternative, modifications, and equivalents, which may be included within the spirit and scope of the claimed subject matter as defined by the appended claims.

Furthermore, in the following detailed description, numerous specific details are set forth in order to provide a thorough understanding of the claimed subject matter. However, it will be recognized by one skilled in the art that embodiments may be practiced without these specific details or with equivalents thereof. In other instances, well-known methods, procedures, components, and circuits have not been described in detail as not to unnecessarily obscure aspects and features of the subject matter.

Portions of the detailed description that follows are presented and discussed in terms of a method. Although steps and sequencing thereof are disclosed in a figure herein describing the operations of this method, such steps and sequencing are exemplary. Embodiments are well suited to performing various other steps or variations of the steps recited in the flowchart of the figures herein, and in a sequence other than that depicted and described herein.

Some portions of the detailed description are presented in terms of procedures, steps, logic blocks, processing, and other symbolic representations of operations on data bits that can be performed on computer memory. These descriptions and representations are the means used by those skilled in the data processing arts to most effectively convey the substance of their work to others skilled in the art. A procedure, computer-executed step, logic block, process, etc., is here, and generally, conceived to be a self-consistent sequence of steps or instructions leading to a desired result. The steps are those requiring physical manipulations of physical quantities. Usually, though not necessarily, these quantities take the form of electrical or magnetic signals capable of being stored, transferred, combined, compared, and otherwise manipulated in a computer system. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussions, it is appreciated that throughout, discussions utilizing terms such as "accessing," "writing," "including," "storing," "transmitting," "traversing," "associating," "identifying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

Some embodiments may be described in the general context of computer-executable instructions, such as program modules, executed by one or more computers or other devices. Generally, program modules include routines, programs, objects, components, data structures, etc. that perform particular tasks or implement particular abstract data types. Typically, the functionality of the program modules may be combined or distributed as desired in various embodiments.

Cyclotron RF Resonator Tuning with Asymmetrical Fixed Tuner

The following description is presented to enable a person skilled in the art to make and use the embodiments of this invention; it is presented in the context of a particular application and its requirements. Various modifications to the disclosed embodiments will be readily apparent to those skilled in the art, and the general principles defined herein may be applied to other embodiments and applications without departing from the spirit and scope of the present disclosure. Thus, the present invention is not limited to the embodiments shown, but is to be accorded the widest scope consistent with the principles and features disclosed herein.

Figure 1:
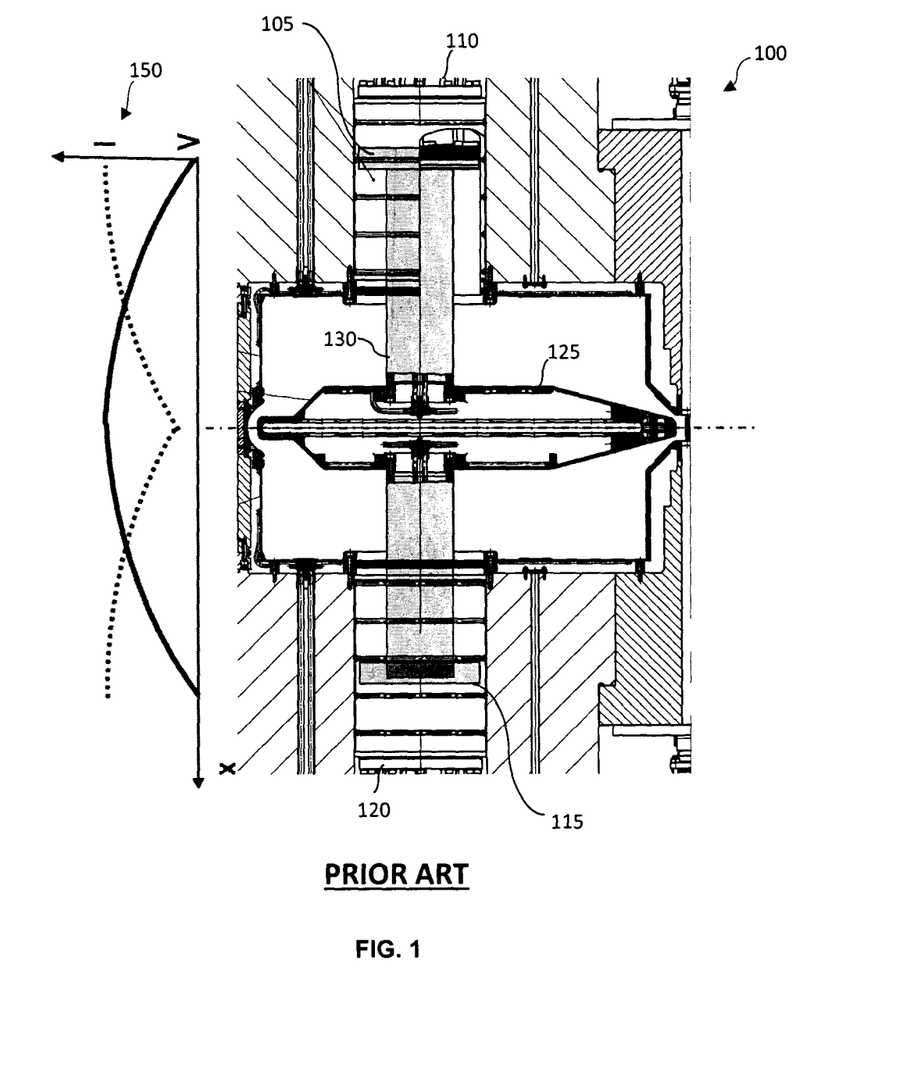
FIG. 1 is a diagram depicting an exemplary cyclotron RF resonator.

With regard to FIG. 1, a diagram of an exemplary cyclotron RF resonator 100 is depicted. Cyclotron RF resonator 100 includes a top shorting plate tuner 105 and a bottom shorting plate tuner 115 disposed inside moveable tuner stem 110 and moveable tuner stem 120, respectively. Moveable tuner stems 120 and 110 further include inner conductor 130 connecting top shorting plate tuner 105 and a bottom shorting plate tuner 110 with dee 125. Dee 125 is positioned between top shorting plate tuner 105 and a bottom shorting plate tuner 115 for performing particle acceleration based on the position of top shorting plate tuner 105 and a bottom shorting plate tuner 115. Top shorting plate tuner 105 and a bottom shorting plate tuner 115 are moved up and down symmetrically in relation to a horizontal axis represented by the dotted line in the middle of dee 125, where bringing the top shorting plate tuner 105 and a bottom shorting plate tuner 115 closer to or further from dee 125 adjusts the resonance frequency of cyclotron RF resonator 100.

Graph 150 of FIG. 1 illustrates the acceleration voltage on the vertical axis (V) in relation to the position of the shorting plate tuners along the horizontal axis (X). At resonance frequency, given from the half wave length, the voltage distribution is depicted in the graph. The highest voltage is on the dashed median plane. At the positions of the shorts the voltage is zero. The graph also illustrates the alternating high frequency currents (I). When the middle region between the shorting plates 105 and 115 does not coincide with the medium plane where the proton beam is accelerated, the voltage maximum does not coincide with the proton beam plane. This leads to a decrease in accelerating efficiency, and in a worst case makes particle acceleration impossible.

Figure 2:
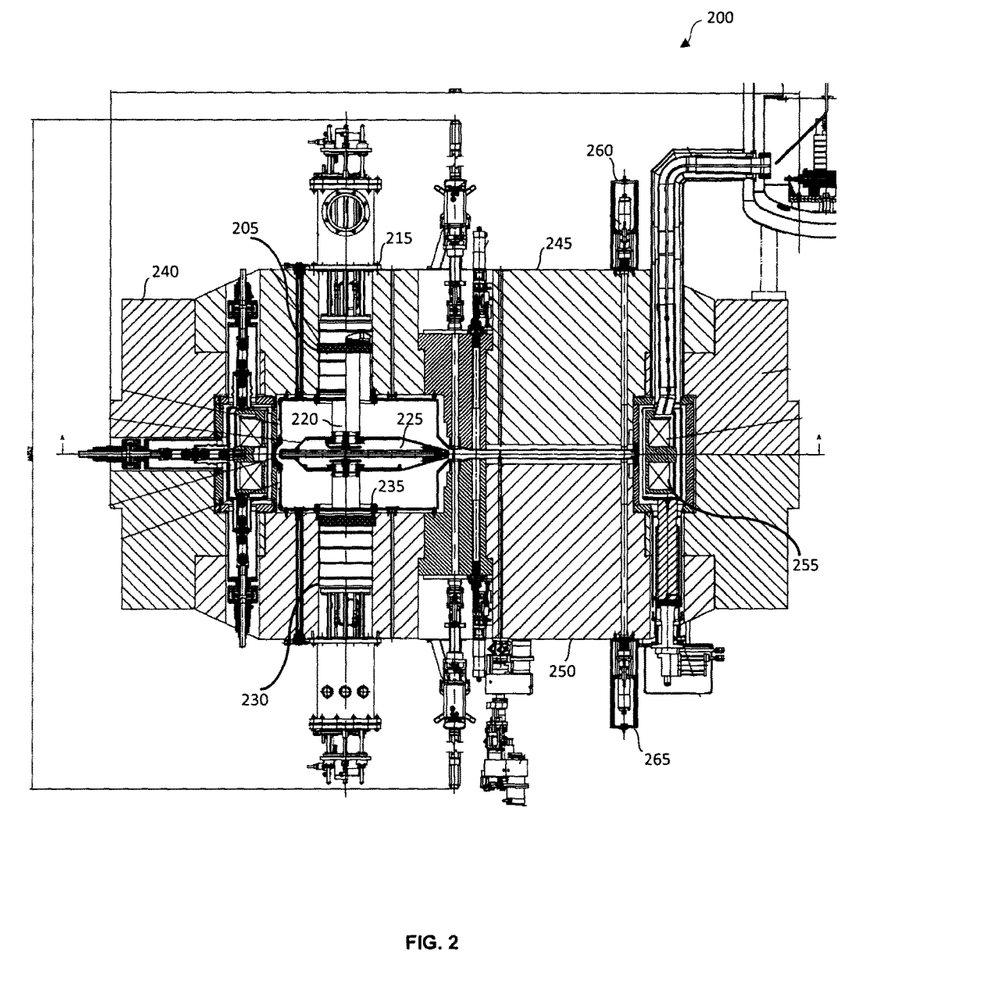
FIG. 2 is a diagram of an exemplary cyclotron using an RF resonator with an asymmetrical tuner depicted according to embodiments of the present invention.

With regard to FIG. 2, a diagram of an exemplary cyclotron 200 including an RF resonator is depicted according to embodiments of the present invention. The cyclotron RF resonator includes a single shorting plate tuner 205 inside moveable tuner stem 215 and a fixed short 235 inside the fixed short stem 230. The design does not require top-bottom mirror symmetry. For small movements in relation to the wavelength, the maximum acceleration voltage is bound by the capacitance of the accelerating surfaces. As such, cyclotron 200 may perform particle acceleration using asymmetrical tuning to reduce design complexity, cost of maintenance, fabrication and installation complexity, failure rate, and software complexity (e.g., control software), for example.

Although the fixed shorting plate 235 and fixed short stem 230 are depicted below dee 225, according to some embodiments, fixed shorting plate 235 and fixed short stem 230 are located in another position (e.g., above dee 225). Fixed short stem 230 further includes inner conductor 220. In some of the embodiments, the voltage distribution does not change, and the voltage maximum remains in middle position despite asymmetrical movement of the shorting plate tuner. Voltage is bound by capacitance of the accelerating surfaces, and a very small distance between dee 225 and an outer structure or liner of the resonator yields a relatively high capacitance.

Cyclotron 200 further includes an iron magnet for shaping a magnetic field, a magnetic coil 255, an upper ion source 260, and a lower ion source 265. Specifically, according to some embodiments, the iron magnet includes iron yoke ring 240, upper iron pole cap 245, and lower iron pole cap 250. The coil and iron components are used to produce and shape the magnetic field needed to accelerate particles inside the cyclotron. Upper pole cap 245 and lower pole cap 250 work in conjunction with yoke ring 240 to return the magnetic field lines. The ion sources 260 and 265 may comprise any particle source that produces charged particles for the accelerator, such as an external ion source with an injection system or an Electron Cyclotron Resonance (ECR) Ion Source.

According to some embodiments, magnetic coil 255 is constructed from annealed copper, insulated with fiber-glass and covered with an epoxy resin.

According to some embodiments, tuner stem 215 comprises a sliding shorting plate. According to other embodiments, tuner stem 215 comprises a bellowed stem. According to other embodiments, tuner stem 215 comprises a telescopic tube.

Figure 3:
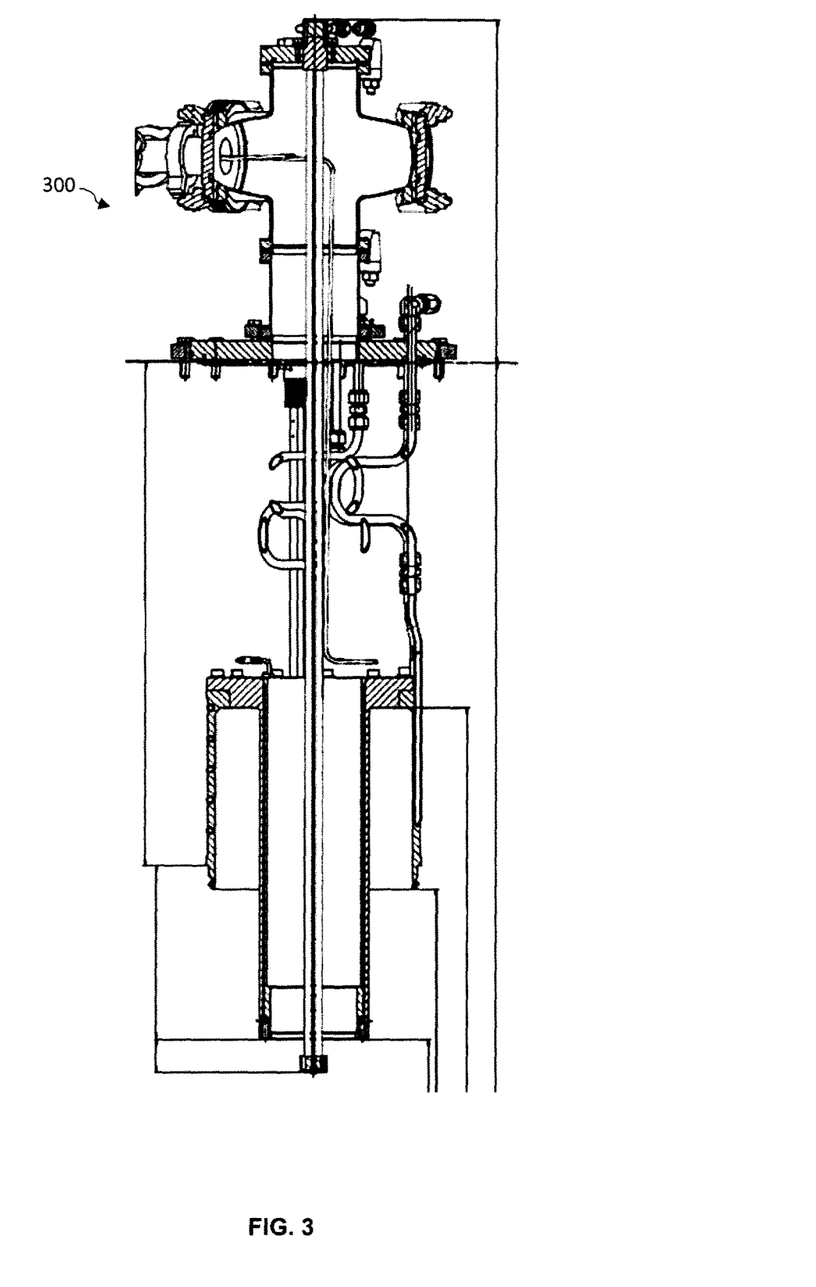
FIG. 3 is a diagram of a sectional view of an exemplary fixed stem comprising a short flange depicted according to embodiments of the present invention.
Figure 4:
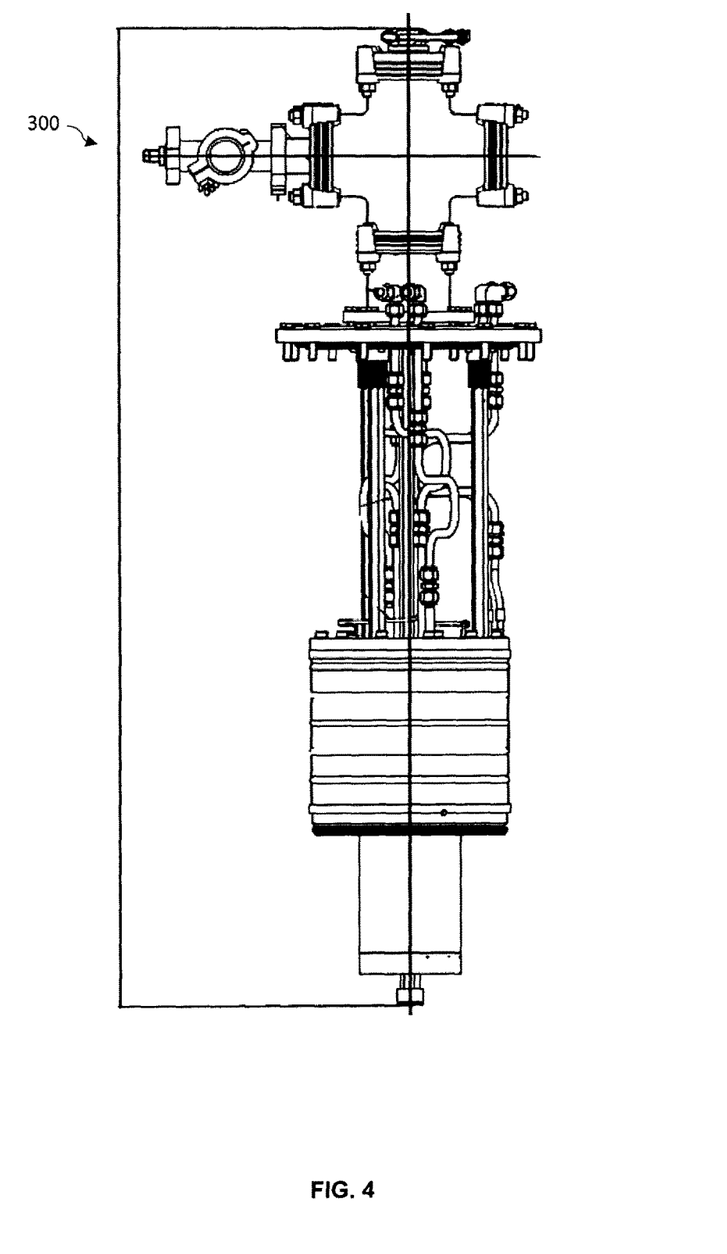
FIG. 4 is a diagram of a back view of an exemplary fixed stem depicted according to embodiments of the present invention.

With regard to FIG. 3, a diagram of a sectional view of an exemplary fixed stem 300 comprising a short flange is depicted according to embodiments of the present invention. FIG. 4 is a diagram of a back view of the exemplary fixed stem 300 depicted according to embodiments of the present invention. Fixed stem 300 is used for performing asymmetrical tuning using an RF cyclotron resonator, and is simpler in design, with fewer moving parts than traditional stem designs. According to some embodiments, the fixed stem 300 comprises no moving parts.

Figure 5:
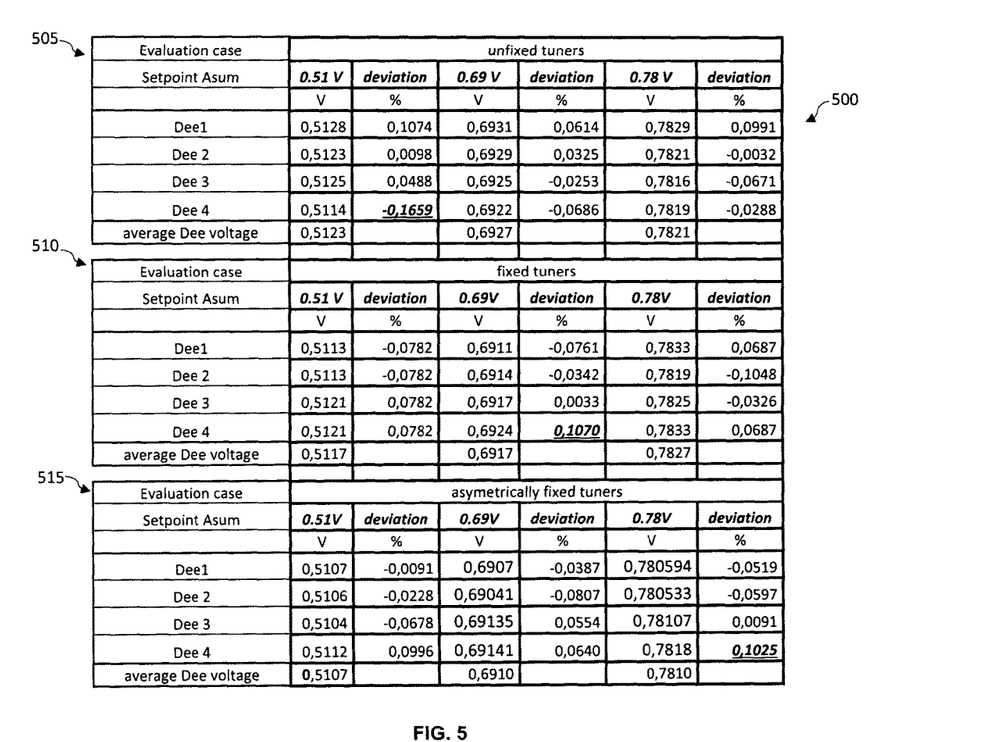
FIG. 5 is a chart of exemplary measurement results from RF cyclotron resonators depicted according to embodiments of the present invention.

With regard to FIG. 5, a chart 500 of exemplary measurement results from RF cyclotron resonators is depicted according to embodiments of the present invention. Evaluation case 505 includes voltage measurements from an RF cyclotron resonator with unfixed tuners. Evaluation case 510 includes voltage measurements from an RF cyclotron resonator with fixed tuners. Evaluation case 515 includes voltage measurements from an RF cyclotron resonator with asymmetrically fixed tuners.

Figure 6A:
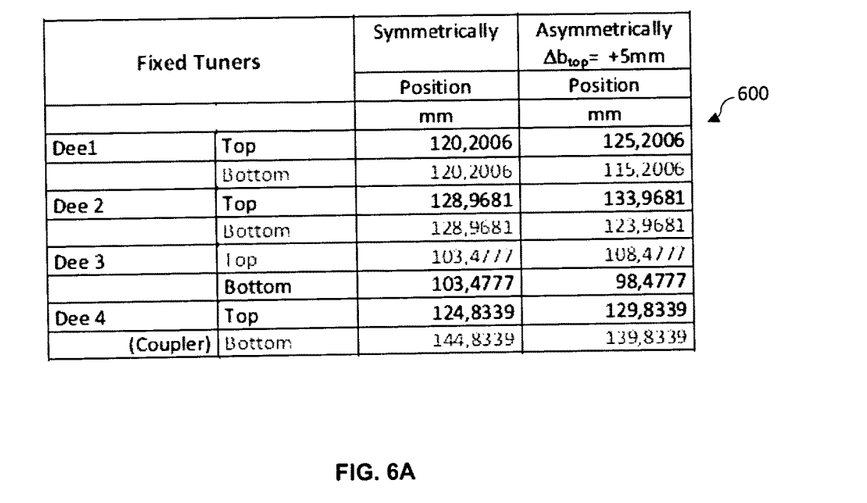
FIG. 6A is a table of positions of exemplary Dees 1-4 at various positions using symmetrical and asymmetrically fixed tuners depicted according to embodiments of the present invention.

With regard to FIG. 6A, a table 600 with exemplary Dees 1-4 at various positions using symmetrical and asymmetrically fixed tuners is depicted according to embodiments of the present invention. Extraction efficiencies of an accelerated beam were observed and a radial beam probe (RBP) scan was used to evaluate a change in the beam centering. As discussed above, embodiments of the present invention do not require top-bottom mirror symmetry. For small movements in relation to the wavelength, the maximum acceleration voltage is bound by the capacitance of the accelerating surfaces.

Like with symmetrically fixed tuners, for asymmetrically fixed tuners, no unusual behavior of the tuner positioning was caused by the field balance loop or the matching loop. At the 14:28 timestamp, half of the tuners are static. At timestamp 14:56, the field balance loop was activated and regulated the dee voltages in balance within five minutes. Regulation behavior from the field balance loop shows no negative effects caused by fixed tuners. Performing particle acceleration using asymmetrical tuning reduces design complexity, the cost of maintenance, fabrication and installation complexity, failure rate, and software complexity (e.g., control software), for example.

Figure 6B:
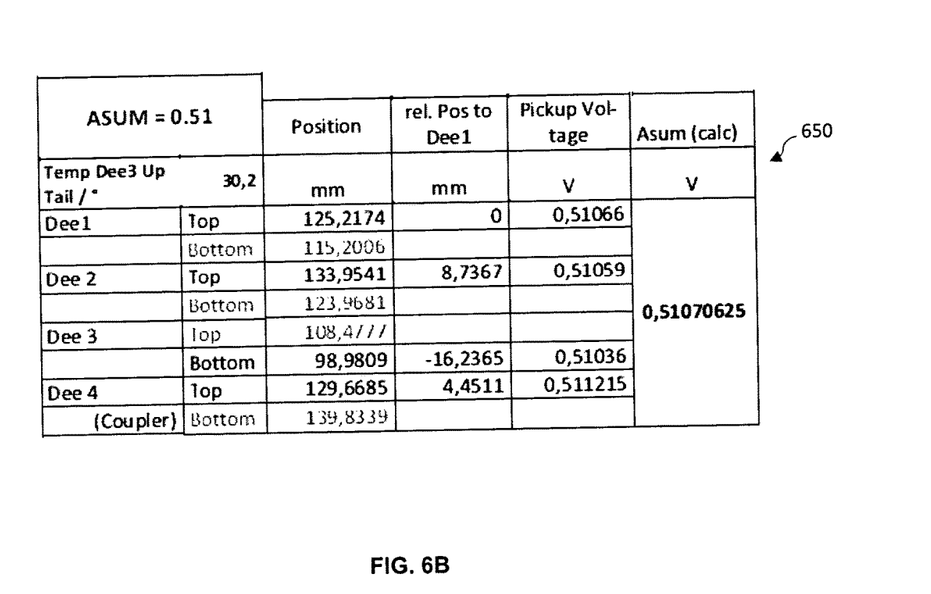
FIG. 6B is a table of shorting plate positions and voltages for an Asum value of 0.51 depicted according to embodiments of the present invention

With regard to FIG. 6B, a table 650 of shorting plate positions for different Asum set points is depicted according to embodiments of the present invention, starting with activating the filed balance loop at 0.51 V Asum. An Asum value indicates the sum of amplitudes for four pickup voltages (one per Dee) divided by four. The Asum value may be considered a mean amplitude. Changes in field balance depicted in FIG. 6B and the reaction of the field balance loop are caused by the iterative increase of the Asum from 0.51 V to 0.57 V, and finally to 0.69 V. After every step the field balance loop took roughly 5-6 minutes to stabilize tuner movement.

For an Asum of 0.51 V, the system took an average of 350 seconds for the tuners to reached stable relative positions after a restart of the RF system to full power. After that time the system reached a balanced field across the dees 1-4. For an Asum of 0.78 V, the System took an average of 350 s until the tuners reached stable positions relative to each other after a restart of the RF system to full power.

Figure 7:
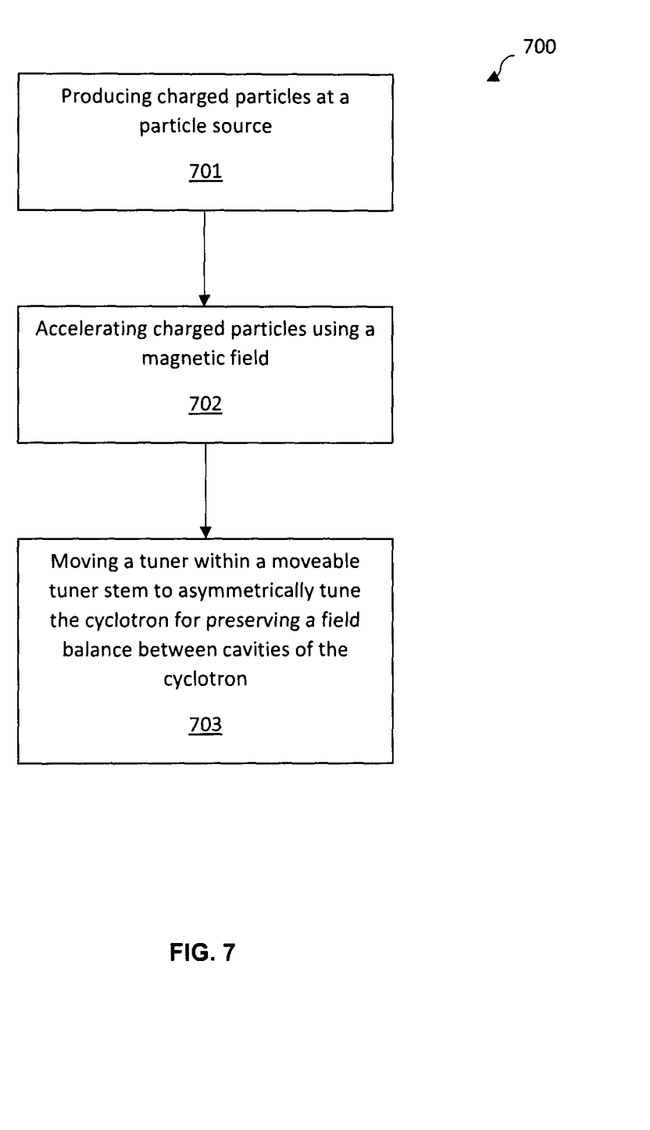
FIG. 7 is a flowchart depicting an exemplary sequence of steps for performing a method of asymmetrically tuning a cyclotron according to embodiments of the present invention.

With regard to FIG. 7, a flowchart 700 depicting an exemplary sequence of steps for asymmetrically tuning a cyclotron is disclosed according to embodiments of the present invention. At step 701, charged particles are produced at a particle source. The particle source may include any particle source that produces charged particles for an accelerator, such as an external ion source with an injection system or an ECR Ion Source, for example.

At step 702, the charged particles are accelerated using a magnetic field. According to some embodiments, the magnetic field is shaped using a magnet, and field lines of the magnet field are returned using an upper pole cap, a lower pole cap, and a yoke ring.

At step 703, a first tuner disposed within a moveable tuner stem is moved to asymmetrically tune the cyclotron for preserving a field balance between cavities of the cyclotron. As described above, a distance between the first tuner and a fixed tuner defines a resonance frequency of the cyclotron, and a maximum field produced by the cyclotron is independent from an asymmetrical movement of the tuner plate.

Embodiments of the present invention are thus described. While the present invention has been described in particular embodiments, it should be appreciated that the present invention should not be construed as limited by such embodiments, but rather construed according to the following claims.

What is claimed is:

1. A cyclotron, comprising:
   a main coil for producing a magnetic field;
   a magnet surrounding the main coil for shaping the magnetic field;
   a fixed short stem coupled to a vacuum chamber disposed within the cyclotron;
   a fixed short disposed within the fixed short stem;
   a single movable tuner stem coupled to the vacuum chamber;
   a single shorting plate tuner disposed within the movable tuner stem, wherein the longitudinal axis of the fixed short stem is aligned with the longitudinal axis of the moveable tuner stem, and wherein the longitudinal axes of the fixed short stem and the moveable tuner stem are orthogonal to the longitudinal axis of the vacuum chamber; and
   a radio frequency resonator for producing an alternating electric field using the vacuum chamber,
   wherein the shorting plate tuner asymmetrically tunes an RF resonator of the cyclotron to accelerate particles based on a distance between the shorting plate tuner and the fixed short, wherein the distance is changed by moving only the moveable tuner stem including the shorting plate tuner relative to the fixed short stem and the fixed short.

2. The cyclotron of claim 1, further comprising an inner conductor inside the fixed short stem disposed between the single shorting plate tuner and the vacuum chamber.

3. The cyclotron of claim 1, wherein a maximum acceleration voltage of the cyclotron is bound by a capacitance of the cyclotron.

4. The cyclotron of claim 1, wherein the fixed short stem comprises only fixed parts.

5. The cyclotron of claim 1, wherein the fixed short stem is disposed above the vacuum chamber.

6. The cyclotron of claim 1, wherein the fixed short stem is disposed below the vacuum chamber.

7. The cyclotron of claim 1, wherein the magnet comprises a top iron magnet, a bottom iron magnet, and an opening between the top iron magnet and the bottom iron magnet disposed on a median plane of the cyclotron.

8. The cyclotron of claim 1, wherein the magnet comprises a yoke ring, a lower pole cap, and an upper pole cap, wherein the yoke ring, the lower pole cap, and the upper pole cap are used to return magnetic field lines of the magnetic field.

9. A fixed short stem for tuning an RF cyclotron resonator, the fixed short stem comprising:
    a short disposed within the fixed short stem; and
    an inner conductor disposed within the fixed short stem and in contact with the short,
    wherein the inner conductor contacts an outer surface of a dee, a single moveable tuner stem comprising a single shorting plate tuner tunes the resonator by changing a distance between the shorting plate tuner and the short, and the dee performs particle acceleration, wherein the longitudinal axis of the fixed short stem is aligned with the longitudinal axis of the moveable tuner stem, and wherein the longitudinal axes of the fixed short stem and the moveable tuner stem are orthogonal to the longitudinal axis of the dee, and wherein the distance is changed by moving only the moveable tuner stem including the shorting plate tuner relative to the fixed short stem and the short.

10. The fixed short stem of claim 9, wherein the resonator produces an acceleration voltage based on the position of the shorting plate tuner.

11. The fixed short stem of claim 9, wherein a maximum acceleration voltage of the cyclotron resonator is bound by a capacitance of the cyclotron resonator.

12. The fixed short stem of claim 9, wherein the fixed short stem comprises only fixed parts.

13. The fixed short stem of claim 9, wherein the shorting plate tuner is disposed above the resonator.

14. The fixed short stem of claim 9, wherein the shorting plate tuner is disposed below the resonator.

15. A cyclotron resonator, comprising:
    a fixed short stem comprising a fixed tuner coupled to a vacuum chamber;
    a single movable tuner stem coupled to the vacuum chamber;
    a resonator dee disposed within the vacuum chamber; and
    a single shorting plate tuner disposed within the movable tuner stem, wherein the shorting plate tuner asymmetrically tunes the cyclotron resonator based on a distance between the fixed tuner and the shorting plate tuner to accelerate particles using an acceleration voltage, wherein the longitudinal axis of the fixed short stem is aligned with the longitudinal axis of the moveable tuner stem, and wherein the longitudinal axes of the fixed short stem and the moveable tuner stem are orthogonal to the longitudinal axis of the vacuum chamber, and wherein the distance is changed by moving only the moveable tuner stem including the shorting plate tuner relative to the fixed short stem and the fixed tuner.

16. A method for asymmetrically tuning a cyclotron, the method comprising: producing charged particles at a particle source; accelerating the charged particles using a magnetic field; and moving a first tuner disposed within a single moveable tuner stem to asymmetrically tune the cyclotron for preserving a field balance between cavities of the cyclotron, wherein a distance between the first tuner and a fixed tuner within a fixed short stem defines a resonance frequency of the cyclotron, wherein the longitudinal axis of the fixed short stem is aligned with the longitudinal axis of the movable tuner stem, and wherein the longitudinal axes of the fixed short stem and the moveable tuner stem are orthogonal to the longitudinal axis of a vacuum chamber, wherein the distance is changed by moving only the moveable tuner stem including the first tuner relative to the fixed short stem and the fixed tuner, and wherein a maximum field produced by the cyclotron is independent from movement of the first tuner.

17. The method of claim 16, wherein the charged particles are used to irradiate a target.

18. The method of claim 16, further comprising shaping the magnetic field using a magnet, wherein field lines of the magnet field are returned using an upper pole cap, a lower pole cap, and a yoke ring.

19. The method of claim 18, wherein the magnet, the upper pole cap, the lower pole cap, and the yoke ring comprise iron.

20. The method of claim 16, wherein a maximum acceleration voltage produced by the cyclotron is bound by a capacitance of accelerating surfaces of the cyclotron.

21. The method of claim 16, wherein the charged particles comprise ions.

22. The method of claim 16, wherein the particle source comprises an external ion source and an injection system.

23. The method of claim 16, wherein the particle source comprises an electron cyclotron resonance (ECR) ion source.

24. The method of claim 16, wherein the fixed tuner is disposed within a fixed tuner stem, and the fixed tuner stem comprises a conductor.

* * * * *